(12) United States Patent
Arbeit et al.

(10) Patent No.: US 6,586,655 B2
(45) Date of Patent: *Jul. 1, 2003

(54) EXPRESSION OF HUMAN ESTROGEN RECEPTORS IN TRANSGENIC MICE

(75) Inventors: Jeffrey M. Arbeit, San Francisco, CA (US); Peter J. Kushner, San Francisco, CA (US); Rosalie M. Uht, San Francisco, CA (US); Birgit Anderegg, San Francisco, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/365,614

(22) Filed: Aug. 2, 1999

(65) Prior Publication Data

US 2003/0056230 A1 Mar. 20, 2003

(51) Int. Cl.[7] .......................... G01N 33/00; A01K 67/00; A01K 67/033; C12N 15/63; C12N 15/85
(52) U.S. Cl. ................... 800/3; 800/3; 435/455
(58) Field of Search ................. 800/9, 10, 18, 800/21, 3; 435/354, 320.1, 252.33, 69.7, 7.23, 325, 455; 536/23.5

(56) References Cited

U.S. PATENT DOCUMENTS

| | | | | |
|---|---|---|---|---|
| 5,709,844 A | * | 1/1998 | Arbeit et al. | 424/9.2 |
| 5,914,265 A | * | 6/1999 | Roop et al. | 435/320.1 |
| 5,962,320 A | * | 10/1999 | Robinson | 435/366 |
| 6,028,245 A | * | 2/2000 | Wasylyk et al. | 800/18 |
| 6,265,173 B1 | * | 7/2001 | Evans et al. | 435/7.1 |

OTHER PUBLICATIONS

SW Curtis et al., Journal of Molecular Endocrinology, "Promoter and species specific differential estrogen–mediated gene transcription in the uterus and cultured cells using structurally altered agonists," 1997, 18, 203–211.*
WR Staggers et al., Gene, "Sequence of the functional human keratin K14 promoter," 1995, 153,297–298.*
Ebert et al, 1988, Molecular Endocrinology, 2: 277–283.*
Hammer et al, 1986, 63: 269–278.*
Houdebine et al, 1994, J. Biotechnol., 34: 269–287.*
Kappel et al, 1992, Cur. Opin. Biotechnol., 3: 548–553.*
Mullins et al, 1996, J. Clin. Invest., 98: S37–S40.*
Strojek and Wagner, 1988, Genetic Engineering: Principles and Methods, 10: 221–246.*
Vasioukhin et al, 1999, PNAS, 96: 8551–8556.*
Wall et al, 1996, Theriogenology, 45: 57–68.*
Lundholt et al, 1996, Mol. Cell. Endocrin., 119: 47–59.*
Pickarz et al, 1993, J. Biol. Chem., 268: 7613–7616.*
Wang et al, 1997, Proc. Natl. Acad. Sci., 94: 219–226.*

* cited by examiner

Primary Examiner—Scott D. Priebe
Assistant Examiner—Michael C. Wilson
(74) Attorney, Agent, or Firm—Townsend and Townsend and Crew

(57) ABSTRACT

The present invention relates to improved compositions and methods for assaying the efficacy of novel drugs functioning either as agonists or antagonists at nuclear receptors. In particular, the invention provides transgenic non-human animals comprising a human steroid hormone receptor gene operably linked to a promoter which directs expression of the steroid hormone receptor gene in an epithelial cell of the non-human animals.

11 Claims, No Drawings

EXPRESSION OF HUMAN ESTROGEN RECEPTORS IN TRANSGENIC MICE

STATEMENT AS TO RIGHTS TO INVENTIONS MADE UNDER FEDERALLY SPONSORED RESEARCH AND DEVELOPMENT

This invention was made with Government support under Grant No. CA71358, awarded by the National Institutes of Health. The Government has certain rights in this invention.

FIELD OF THE INVENTION

This invention pertains to the field of transgenic non-human animals. In particular this invention pertains to transgenic animals that express human steroid hormone receptor genes in desired tissues, such as the epithelium, and to methods of screening potential therapeutics for activity at steroid hormone receptors.

BACKGROUND OF THE INVENTION

Steroid hormones are secreted by the adrenal cortex, testis, ovary and placenta and include the androgens (such as testosterone), estrogens (such as estradiol and estrone), glucocorticoids (cortisone, corticosterone, and cortisol), mineralocorticoids (primarily aldosterone), and progestogens (primarily progesterone). Steroid hormones regulate proliferation and differentiation in target cells within the reproductive tract, mammary gland, and peripheral tissues such as the bones, heart, blood vessels, and hair follicles (for a review, see Yamashita et al., *Localization and functions of steroid hormone receptors,* 1998, *Histol. Histopathol.* 13(1):255–70).

Steroid hormones are highly lipophilic and act through nuclear receptors rather than through receptors on the plasma membrane. Steroid hormone receptors have been shown to support the development of cancer in the breast, prostate, uterus, cervix, and ovaries. In addition, steroid hormone receptors appear to prevent osteoporosis of the bones, to prevent atherosclerosis of the coronary arteries of the heart, and to mediate baldness in men. Therefore, steroid hormone nuclear receptors and other gene products that are involved in steroid hormone metabolism are attractive targets for the development of therapeutics that address the treatment of reproductive cancers and conditions such as osteoporosis, atherosclerosis, and baldness.

Steroid hormone receptors are part of a family of nuclear receptors which contain a hormone-biding region and a DNA-binding region, and thereby act as transcription enhancers. Upon binding to their specific ligands, nuclear receptors interact directly with regions of DNA in order to influence transcription of genes regulating hormonal activity. See, Ribeiro et al., *The nuclear hormone receptor gene superfamily,* 1995, *Annual Rev Med.* 46:443–53. There is a growing list of drugs that either bind directly to steroid hormone receptors or modulate steroid hormone metabolism. Drugs that bind directly to the nuclear receptors include tamoxifen, an anti-estrogen used in treatment of breast cancer, and raloxifene, used in prevention of osteoporosis. Drugs that modulate sex steroid metabolism include aromatase inhibitors, used to treat breast cancer and possibly prostate cancer, and finasteride (Propecia™), used in the treatment of hair loss.

Models of targeted expression of oncogenes and growth factors to the epidermis of transgenic mice have been described. These models have used keratin promoters to target the expression of foreign DNA. The basal cell specific keratin-14 (K14) promoter has been used to express growth factors and oncogenes in transgenic animals as models for the development of specific carcinomas (Vassar et al., 1991, *Cell* 64:365–380; U.S. Pat. No. 5,698,764). There is currently no transgenic model for the expression of human nuclear receptors in the epithelium.

Despite the existence of several drugs that either bind directly to steroid hormone receptors or modulate steroid hormone metabolism, there is a further need to develop models for assaying and testing the site of action and the efficacy of drugs that act to modulate nuclear receptor activity and metabolism. The present invention addresses these and other needs.

SUMMARY OF THE INVENTION

The present invention provides transgenic non-human animals exhibiting a detectable phenotype, typically epidermal hyperplasia, caused by a steroid hormone receptor gene operably linked to a promoter which directs expression of the steroid receptor gene in the epithelium in the non-human animal, preferably a mouse. The steroid receptor gene is preferably a human estrogen receptor gene. The promoter used to drive expression of the steroid receptor gene is preferably a keratin-14 promoter directing expression of the steroid receptor in a basal keratinocyte.

The animal may further comprise a β-galactosidase gene operably linked to a promoter which directs expression of the β-galactosidase gene in an epithelial cell. If the steroid hormone receptor gene is expressed in a basal keratinocyte, the β-galactosidase gene is also preferably expressed in a basal keratinocyte.

The invention also provides DNA constructs comprising an expression cassette including a steroid hormone receptor gene operably linked to a promoter which directs expression of the steroid hormone receptor in the epithelium, preferably in a basal keratinocyte. The promoter is preferably the keratin-14 promoter.

The invention further provides methods of testing a composition for the ability to modulate steroid hormone receptor activity. The methods comprise providing a transgenic non-human animal comprising a human steroid hormone receptor gene operably linked to a keratin-14 promoter which directs expression of the gene in an epithelial cell, administering the composition to the non-human animal, and detecting changes in the epithelial cell of the non-human animal.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, "non-human animals" include, for example, mammals such as non-human primates, ovine, canine, bovine, rattus and murine species, as well as rabbits and the like. Preferred non-human animals are selected from the rodent family, including rat, guinea pig and mouse, most preferably mouse.

As used herein, a "steroid" or "steroid hormone" refers to any one of a group of biologically active compounds synthesized from cholesterol that contain a cyclopentanoperhydrophenanthrene nucleus. A "steroid receptor" or "steroid hormone receptor" is a nuclear receptor that binds a steroid or steroid hormone described herein.

As used herein, the term "steroid hormone receptor gene" or "steroid receptor gene" refers to a nucleotide sequence, or any subsequence thereof, that encodes a steroid receptor described herein or that encodes a gene product exhibiting DNA-binding and steroid hormone-binding activity, in vitro or in vivo; and any conservatively modified variants thereof. Also explicitly included within this definition are both wild-type and mutant genes (e.g. mutant steroid hormone receptor genes isolated from cancer cells) that may or may not have altered activity as compared to wild-type genes.

The term "estrogen receptor" refers to a known nuclear receptor having a predicted molecular weight of about 66-kd, that is activated by estrogenic steroid hormones such as estradiol. The active form of the protein enhances expression of genes involved in the formation of secondary sexual characteristics in mammalian females. An estrogen receptor can be an allele, polymorphic variant, interspecies homolog, or any subsequence thereof that exhibits estrogenic steroid hormone-binding activity.

As used herein, "estrogen receptor gene" is a wild-type or mutant nucleotide sequence that encodes an estrogen receptor described herein, and conservatively modified variants thereof. An example of an estrogen receptor gene is described in Greene et al., 1986, *Science* 231(4742):1150–4. One of ordinary skill in the art will recognize that certain modifications, additions, and deletions may be made to the estrogen receptor gene sequence which will not affect the function or activity of the gene product. Such variants are included within this definition. An example of a mutant estrogen receptor gene is K206A, in which the lysine at position 206 is replaced by alanine.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence. For example, a promoter is operably linked to a coding sequence if it controls transcription of the sequence.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

An "expression cassette" is a nucleic acid construct, generated recombinantly or synthetically, with a series of specified nucleic acid elements that permit transcription of a particular nucleic acid in a host cell. The expression cassette can be part of a plasmid, virus, or nucleic acid fragment. Typically, the expression vector includes a nucleic acid to be transcribed operably linked to a promoter.

A "detectable phenotype" is any symptom or characteristic of an organism which is measurable by any one or a number of different objective criteria, including, but not limited to, visual inspection, microscopic observation, antibody labeling, DNA labeling, or assays for changes in gene expression which are known in the art. Detectable phenotypes may include, but are not limited to, skin thickening, redness, flaking, epidermal hyperplasia, dysplasia, altered nuclear labeling, or altered protein or gene expression.

The term "modulate the activity" means to have an effect on, e.g., to increase or inhibit or otherwise alter, the activity of, e.g., a human nuclear receptor gene.

The term "administering" the composition means contacting by any conventional method known to one of skill in the art, such as, for example, parenteral, oral, topical, and inhalation routes.

The phrase "detecting changes" refers to using one or a number of different objective criteria, including, but not limited to, visual inspection, microscopic observation, antibody labeling, DNA labeling, or assays for changes in gene expression which are known in the art, to determine the effect of a composition on a non-human animal of the invention.

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 70%, more preferably 80%, most preferably 90–95% nucleotide or amino acid residue identity when aligned for maximum correspondence over a comparison window as measured using one of the following sequence comparison algorithms or by manual alignment and visual inspection: This definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403–410 and Altschuel et al. (1977) *Nucleic Acids Res.* 25: 3389–3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Lower stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

DESCRIPTION OF THE SPECIFIC EMBODIMENTS

I. Introduction

Steroid hormones are associated with the development of breast, prostate, uterine, cervical, and ovarian cancer. In addition, steroid hormones mediate baldness in men, and are important in the prevention of osteoporosis, and atherosclerosis of the coronary arteries of the heart. Steroid hormone activity is mediated by nuclear steroid hormone receptors. Therefore, steroid hormone receptors and other proteins involved in steroid hormone metabolism are attractive targets for the development and testing of therapeutics that address the treatment of reproductive cancers and conditions such as osteoporosis, atherosclerosis, and baldness.

The present invention provides transgenic animals and DNA constructs for targeting steroid hormone receptor genes to the epithelium of transgenic animals which exhibit an easily observable phenotype. Alternatively, the receptor genes can be targeted to the various tissues in which these cancers occur (e.g. breast, prostate, uterine, cervical and ovarian tissues). These animals, e.g., mice, provide a convenient assay to evaluate the effect of compositions that function either as agonists or antagonists of the target steroid hormone receptors and metabolizing enzymes. The present invention is thus useful in the testing of potential therapeutic drugs that target either steroid hormone receptors or other genes that are involved in the metabolism of steroid hormones, e.g, genes encoding enzymes such as aromatase. For example a test compound can first be evaluated in a transgenic animal in which the steroid hormone receptor gene is targeted to the epithelium and then tested further in an animal in which the gene is targeted to a desired tissue, e.g. breast, in the case of screens for compounds useful in treating breast cancer.

Generally, the nomenclature used hereafter and the laboratory procedures in molecular genetics described below are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general and specific references which are provided throughout this document. The procedures therein are believed to be well known in the art and are provided for the convenience of the reader. Much of the nomenclature and general laboratory procedures described below can be found in Sambrook, et al., *Molecular Cloning—A Laboratory Manual* (2nd Ed.), Vol. 1–3, Cold Spring Harbor Laboratory, Cold Spring Harbor, N.Y., 1989.

II. DNA Constructs

Appropriate constructs for production of vectors used to make transgenic animals are described in Hogan et al., 1986, *Manipulating the Mouse Embryo,* Cold Spring Harbor Laboratory, Cold Spring Harbor, N.Y. In the construction of vectors for the production of transgenic animals, the coding sequence of interest is typically operably linked to expression regulatory sequences. In such transgenes, the expression regulatory sequence is at least the minimal sequences required for efficient cell-type specific expression, which generally are at least a promoter and at least about 1 kilobase (kb) upstream of the promoter. Usually the sequences upstream of the promoter are used contiguously, although various deletions and rearrangements can be employed. Some desired regulatory elements (e.g., enhancers, silencers) may be relatively position-insensitive, so that the regulatory element will function correctly even if positioned differently in a transgene than in the corresponding germline gene. For example, an enhancer may be located at a different distance from a promoter, in a different orientation, and/or in a different linear order. For example, an enhancer that is located 3' to a promoter in germline configuration might be located 5' to the promoter in a transgene.

Typically, expression regulation sequences are chosen to produce tissue-specific or cell type-specific expression of the desired structural gene. In the present invention the targeted cells are, e.g., breast, prostate, uterine, cervical, ovarian or epithelial cells. Once a tissue or cell type is chosen for expression, expression regulation sequences are chosen. Generally, such expression regulation sequences are derived from genes that are expressed primarily in the tissue or cell type chosen. Preferably, the genes from which these expression regulation sequences are obtained are expressed substantially only in the tissue or cell type chosen, although secondary expression in other tissue and/or cell types is acceptable if expression of the recombinant DNA in the transgene in such tissue or cell type is not detrimental to the transgenic animal.

The constructs will usually also comprise downstream expression regulation sequences to supplement tissue or cell-type specific expression. The downstream expression regulation sequences include polyadenylation sequences (either from the endogenous gene or from other sources such as SV40) and sequences that may affect RNA stability as well as enhancer and/or other sequences which enhance expression.

In some embodiments of the present invention, a steroid hormone receptor gene is placed in an expression cassette under the control of a promoter that will direct expression of the gene to an epithelial cell. A number of suitable promoters can be used to direct expression of the steroid hormone nuclear receptor gene in epithelial cells. Particularly useful for targeting the expression of sequences to epithelial cells are the promoters from genes encoding keratin. Keratins are proteins that are expressed in epithelial tissues. Specific keratin proteins, identified by a number, e.g., keratin-5, are exclusively expressed not only in certain epithelia, but also in selected cells populating the epithelia. The epidermis is composed of layers of cells (keratinocytes) which produce specific types of keratin proteins. The basal cells produce keratin 5 and 14 (K5 and K14), whereas the more mature, terminally differentiated keratinocytes, e.g., the suprabasal keratinocytes, produce K10 and K1. Promoters from other keratin genes, such as K8 and K19 are useful in directing expression to epithelia in the bladder or intestines.

In a preferred embodiment, a basal cell keratin promoter (e.g., K5 or K14) is utilized. The K14 promoter is particularly preferred. A K14 expression cassette, containing 2 kb of the K14 promoter/enhancer and 500 bp of the 3' flanking sequence including the K14 polyadenylation signal, has been shown to appropriately target expression of transgenes to the basal cells of squameous epithelium (Vassar et al., 1991, *Cell* 64:365–380; Cheng et al., 1992 *Genes Dev.* 6:1444–1456; Guo et al., 1993, *EMBO J.* 12:973–986; Turksen et al., 1992, *Proc. Natl. Acad. Sci. USA* 89:5068–5072; Vassar et al., 1989, *Proc. Natl. Acad. Sci. USA* 86:1563–1567; U.S. Pat. No. 5,698,764). This cassette is preferred for construction of the transgene of the present invention.

Alternatively, the steroid hormone receptor genes can be targeted to other tissues, such as breast, prostate, uterine, cervical, and ovarian tissue. Promoters for expression in these tissues are known to those of skill. Examples of suitable promoters include the mouse mammary tumor virus (MMTV) promoter (see, e.g. Guy et al. *Mol. Cell. Biol.* 12:954–961 (1992)) for expression in breast tissue and the probasin promoter for expression in prostate cells (see, e.g. Yan et al. *Prostate* 32:129–130 (1997))/

In preferred embodiments, steroid hormone receptor genes are used in the DNA constructs of the invention. One of skill will recognize that the genes need not be naturally occurring wild-type genes, but can be conservatively modified variants or mutants. The human estrogen receptor (ER) gene is conveniently used. See Greene et al., *Sequence and expression of human estrogen receptor complementary DNA,* 1986, *Science* 231(4742):1150–4. One mutant ER gene that can be used is the K206A mutant, in which the lysine at position 206 is substituted with alanine. One of skill in the art will recognize that any other steroid hormone receptor gene can be substituted. For example, the androgen, progesterone, mineralocorticoid, and glucocorticoid receptor genes can conveniently be substituted. See, e.g., Lubahn et al., *The human androgen receptor: complementary deoxyribonucleic acid cloning, sequence analysis and gene expression in prostate,* 1988, *Mol Endocrinol.* 2(12):1265–75; Misrahi et al., *Complete amino acid sequence of the human progesterone receptor deduced from cloned cDNA,* 1987, *Biochem Biophys Res Commun.* 143(2):740–8; Arriza et al., *Cloning of human mineralocorticoid receptor complementary DNA: structural and functional kinship with the glucocorticoid receptor,* 1987, *Science* 237(4812):268–75; Govindan et al., *Cloning of the human glucocorticoid receptor cDNA,* 1985, *Nucleic Acids Res.* 13(23):8293–304.

Further, genes encoding metabolizing enzymes that regulate steroid hormones are suitable targets for the DNA constructs and transgenic animals of the invention. For example, the gene encoding aromatase, an enzyme that converts androgens to estrogen, is conveniently substituted. See, Harada et al., *Cloning of a complete cDNA encoding human aromatase: immunochemical identification and sequence analysis,* 1988, Biochem Biophys Res Commun. 156(2):725–32. Aromatase inhibitors are used to treat breast cancer patients. The recent discovery of a distinct gene for another estrogen receptor (estrogen receptor-beta) suggests that prostate cancer may respond to aromatase inhibitors as well. Chang et al., *Estrogen receptor-beta: implications for the prostate gland,* 1999, Prostate 40(2):115–24.

Methods of modifying the DNA constructs of the invention are well known to those of skill in the art (see, for example, Sambrook et al., 1989 supra; *Methods in Enzymology,* 1987, Vol. 152: *Guide to Molecular Cloning Techniques,* Berger and Kimmel, eds., San Diego, Academic Press, Inc.; or Ausubel et al., 1987, *Current Protocols in Molecular Biology,* Greene Publishing and Wiley-Interscience, N.Y.).

III. Production of Transgenic Animals

The transgenic non-human animals of the invention are produced by introducing expression cassettes comprising the desired promoted and structural gene (e.g. K14-estrogen receptor transgene) into the germline of the non-human animal. In a preferred embodiment, the transgenic non-human animal is selected from the rodent family, including rat, guinea pig and mouse. Most preferably, the transgenic animal is a mouse. The transgenic animal may also be a non-human primate, a member of the ovine, canine, or bovine species, or a rabbit and the like.

In preferred embodiments two expression cassettes are introduced into the animal. One cassette comprises the recombinant expression cassette of the invention and the other comprises a selectable marker gene such as β-galactosidase or β-glucuronidase (GUS), useful in monitoring expression of the transgene. Genes encoding β-galactosidase are particularly preferred. Embryonic target cells at various developmental stages can be used to introduce transgenes. Different methods are used depending on the stage of development of the embryonic target cell.

A. MicroInjection Methods

Microinjection is a preferred method for transforming a zygote or early stage embryo. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster, et al., 1985, *Proc. Natl. Acad. Sci. USA* 82: 4438–4442). As a consequence, all cells of the transgenic non-human animal will carry the incorporated transgene. This will, in general, also be reflected in the efficient transmission of the transgene to offspring of the founder since 50% of the germ cells will harbor the transgene.

The gene sequence being introduced need not be incorporated into a self-replicating plasmid or virus (Jaenisch, 1988, *Science,* 240: 1468–1474). However, in a preferred embodiment, the gene sequence will be introduced in a as a cassette comprising the gene under the control of a promoter. The promoter acts to regulate transcription of the gene in response to endogenous factors present in a particular tissue and thus results in tissue-specific expression of the gene.

Once the DNA molecule has been injected into the fertilized egg cell, the cell is implanted into the uterus of a recipient female, and allowed to develop into an animal. Since all of the animal's cells are derived from the implanted fertilized egg, all of the cells of the resulting animal (including the germ line cells) shall contain the introduced gene sequence. If, as occurs in about 30% of events, the first cellular division occurs before the introduced gene sequence has integrated into the cell's genome, the resulting animal will be a chimeric animal.

By breeding and inbreeding such animals, it has been possible to produce heterozygous and homozygous transgenic animals. Despite any unpredictability in the formation of such transgenic animals, the animals have generally been found to be stable, and to be capable of producing offspring which retain and express the introduced gene sequence.

The success rate for producing transgenic animals is greatest in mice. Approximately 25% of fertilized mouse eggs into which DNA has been injected, and which have been implanted in a female, will become transgenic mice. A number of other transgenic animals have also been produced. These include rabbits, sheep, cattle, and pigs (Jaenisch, 1988, *Science* 240: 1468–1474; Hammer et al., 1986, *J. Animal Sci,* 63: 269; Hammer et al., 1985, *Nature* 315: 680; Wagner et al., 1984 *Theriogenology* 21: 29).

B. Retroviral Methods

Retroviral infection can also be used to introduce a transgene into a non-human animal. The developing non-human embryo can be cultured in vitro to the blastocyst stage. During this time, the blastomeres can be targets for retroviral infection (Jaenich, 1976, *Proc. Natl. Acad. Sci USA* 73: 1260–1264). Efficient infection of the blastomeres is obtained by enzymatic treatment to remove the zona pellucida (Hogan, et al., 1986, In *Manipulating the Mouse Embryo,* Cold Spring Harbor Laboratory Press, Cold Spring Harbor, N.Y.). The viral vector system used to introduce the transgene is typically a replication-defective retrovirus carrying the transgene (Jahner, et al., 1985, *Proc. Natl. Acad. Sci. USA* 82, 6927–6931; Van der Putten, et al., 1985, *Proc. Natl. Acad. Sci. USA* 82, 6148–6152). Transfection is easily and efficiently obtained by culturing the blastomeres on a monolayer of virus-producing cells (Van der Putten, supra ; Stewart et al., 1987, *EMBO J.,* 6: 383–388). Alternatively, infection can be performed at a later stage. Virus or virus-producing cells can be injected into the blastocoele (Jahner et al., 1982, *Nature,* 298: 623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner et al., 1982, supra).

C. ES Cell Implantation

A third target cell for transgene introduction is the embryonic stem cell (ES). ES cells are obtained from pre-implantation embryos cultured in vitro (Evans et al., 1981, *Nature,* 292: 154–156; Bradley, et al., 1984, *Nature,* 309: 255–258; Gossler, et al., 1986, *Proc. Natl. Acad. Sci USA* 83:, 9065–9069; and Robertson, et al., 1986, *Nature,* 322: 445–448). Transgenes can be efficiently introduced into ES cells using a number of means well known to those of skill in the art. Such transformed ES cells can thereafter be combined with blastocysts from a non-human animal. The ES cells thereafter colonize the embryo and contribute to the germ line of the resulting chimeric animal (for a review see Jaenisch, 1988, *Science,* 240: 1468–1474).

In a preferred embodiment, the DNA is introduced by electroporation (Toneguzzo et al., 1988, *Nucleic Acids Res.,* 16: 5515–5532; Quillet et al., 1988, *J. Immunol.,* 141: 17–20; Machy et al., 1988, *Proc. Nat'l. Acad. Sci. USA,* 85: 8027–8031). After permitting the introduction of the DNA molecule(s), the cells are cultured under conventional conditions, as are known in the art.

In order to facilitate the recovery of those cells which have received the DNA molecule containing the desired gene sequence, it is preferable to introduce the DNA containing the desired gene sequence in combination with a second gene sequence which would contain a detectable marker gene sequence. For the purposes of the present invention, any gene sequence whose presence in a cell permits one to recognize and clonally isolate the cell may be employed as a detectable (selectable) marker gene sequence. The presence of the detectable (selectable) marker sequence in a recipient cell may be recognized by PCR, by detection of radiolabelled nucleotides, or by other assays of detection which do not require the expression of the detectable marker sequence. Typically, the detectable marker gene sequence will be expressed in the recipient cell, and will result in a selectable phenotype. Selectable markers are well known to those of skill in the art. Some examples include the hprt gene (Littlefield, 1964, *Science* 145: 709–710), the tk (thymidine kinase) gene of herpes simplex virus (Giphart-Gassler et al., 1989, *Mutat, Res.,* 214: 223–232), the nDtII gene (Thomas et al., 1987, *Cell,* 51: 503–512; Mansour et al., 1988, *Nature* 336: 348–352), or other genes which confer resistance to amino acid or nucleoside analogues, or antibiotics, etc.

Any ES cell may be used in accordance with the present invention. It is, however, preferred to use primary isolates of ES cells. Such isolates may be obtained directly from embryos such as the CCE cell line disclosed by Robertson, E. J., 1989, In: *Current Communications in Molecular Biology,* Capecchi, M. R. (ed.), Cold Spring Harbor Press, Cold Spring Harbor, N.Y., pp. 39–44), or from the clonal isolation of ES cells from the CCE cell line (Schwartzberg et al., 1989, *Science* 212: 799–803). Such clonal isolation may be accomplished according to the method of Robertson, 1987, In: *Teratocarcinomas and Embryonic Stem Cells: A Practical Approach,* E. J. Robertson, Ed., IRL Press, Oxford. The purpose of such clonal propagation is to obtain ES cells which have a greater efficiency for differentiating into an animal. Clonally selected ES cells are approximately 10-fold more effective in producing transgenic animals than the progenitor cell line CCE.

D. Verification of the Presence of the Transgene in the Animal

A number of methods used to detect particular polynucleotide sequences can be used to verify that the desired sequences have been integrated into the genome of the transgenic animal. For instance, Fluorescent In Situ Hybridization (FISH) can be used to detect the transgene in tissue from the animal. Several guides to FISH techniques are available, e.g., Gall et al,. 1981, *Meth. Enzymol.,* 21:470–480, and Angerer et al., 1985, in *Genetic Engineering: Principles and Methods* Setlow and Hollaender, Eds. Vol 7, pg. 43–65. Alternatively, DNA or RNA can be isolated for tissue (typically tail tissue). The desired sequences can be detected by Southern or Northern hybridization or by PCR using primers and probes specific for the transgene. Standard PCR methods useful in the present invention are described in *PCR Protocols: A Guide to Methods and Applications* (Innis et al., eds., Academic Press, San Diego 1990).

Alternatively, expression of the integrated gene can also be detected by detecting the gene product. The protein can be detected, for instance, using standard immunoblotting techniques, well known to those of skill in the art.

IV. Methods to Evaluate the Efficacy of Compositions Functioning at Steroid Hormone Receptors A valuable feature of the transgenic animals of the invention is an easily observable phenotype in the epidermis of the transgenic animal. In some embodiments, the non-human transgenic animals exhibit epidermal hyperplasia. They may alternatively, or in addition, exhibit other phenotypes, including, but not limited to, thickening (acanthosis), redness (erythema), or flaking (hyperkeratosis). Therefore, the transgenic animals of the invention are useful in methods for screening drugs and treatments designed to target nuclear steroid hormone receptors and other proteins involved in steroid hormone metabolism.

The methods herein provided for testing a composition comprise providing a transgenic non-human animal comprising a human steroid hormone receptor gene operably linked to a keratin-14 promoter, administering the composition to the non-human animal, and detecting changes in the epidermis of the non-human animal. The compositions that are tested by this method will depend on the target transgene of the transgenic animal. For example, the K14-estrogen receptor mouse of the invention can be used to assay the efficacy of anti-estrogen drugs, such as tamoxifen, raloxifen, and the like. Similarly, a transgenic animal expressing a K14-androgen receptor transgene in hair follicles can be used to assay drugs directed at androgen receptors for the treatment of baldness. Still further, a transgenic animal comprising a transgene encoding an enzyme involved in steroid hormone metabolism can be used to assay drugs thought to modulate sex steroid metabolism. Examples of such drugs include aromatase inhibitors, and fenesteride (Propesia™), which blocks an enzyme that converts testosterone into the related hormone dihydrotestosterone.

In a preferred embodiment, the epithelium of the epidermis of the transgenic animal is used as a readout to detect changes in the transgenic animal and evaluate the efficacy of compositions functioning either as agonists or antagonists at nuclear receptors and other proteins involved in steroid hormone metabolism. The advantage of using the epidermis as an assay is that it can be conveniently evaluated by a number of different visual and microscopic objective criteria, as well as by molecular assays. For example, the epidermis can be visually inspected for changes such as thickening (acanthosis), redness (erythema), and flaking (hyperkeratosis). In addition, the skin can be evaluated microscopically for hyperplastic thickening and alterations of appearance which are consistent either with normal differentiation, or with dysplasia, such as the persistence of immature neoplastic cells in the upper epidermal layers. At the molecular level, panels of keratin antibodies exist which can identify the keratin expression patterns of transgenic versus non-transgenic epidermis, as each layer of the epidermis produces a repertoire of keratin intermediate filaments specific for cell types within that layer. Still further, the DNA labeling pattern of epidermis is distinct and can be used to compare the number of labeled nuclei from transgenic and non-transgenic epidermis.

V. EXAMPLES

K-14-ER Transgenic Mice

Standard techniques were used to microinject a DNA construct comprising the human estrogen receptor (ER) linked to the enhancer/promoter of the human keratin-14 (K14) gene into B6D2/F2 mouse embryos. Vector construction, production of transgenic animals, and verification of the presence of the transgene in animals were performed generally by the method of Arbeit et al., 1994, *J Virol.* 68(7):4358–68, and U.S. Pat. No. 5,698,764.

Keratin-14-estrogen receptor (K14-ER) mice exhibited striking changes in the skin. Specifically, K14-ER mice developed red (erythematous) ears that were also visibly thickened. Microscopically these ears displayed an increase in the number of cell layers within the epidermis (epidermal hyperplasia), increased synthesis of new DNA, and increased blood vessel formation. This phenotype is stable through at least 2 subsequent generations of progeny K14-ER transgenic mice derived from the founder.

Although the foregoing invention is described in some detail by way of illustration and example for purposes of clarity of understanding, it will be readily apparent to one of ordinary skill in light of the teachings of this invention that a variety of noncritical parameters could be changed or modified to yield essentially similar results without departing from the spirit or scope of the appended claims.

All publications and patent applications cited in this specification are herein incorporated by reference as if each individual publication or patent specification were specifically and individually indicated to be incorporated by reference.

What is claimed is:

1. A transgenic mouse whose genome comprises a human estrogen receptor gene operably linked to a human keratin-14 promoter, whereby expression of the human estrogen receptor gene in an epithelial cell causes a phenotype selected from the group consisting of epidermal hyperplasia and erythematous ears.

2. The transgenic mouse of claim 1, wherein said expression of the human estrogen receptor gene causes epidermal hyperplasia.

3. The transgenic mouse of claim 1, wherein said expression of the human estrogen receptor gene causes erythematous ears.

4. A method of testing a composition for the ability to modulate the activity of a human estrogen receptor, the method comprising:

providing a transgenic mouse whose genome comprises a human estrogen receptor gene operably linked to a human keratin-14 promoter which directs expression of the estrogen receptor in an epithelial cell, whereby expression of the human estrogen receptor gene causes a phenotype selected from the group consisting of epidermal hyperplasia and erythematous ears;

administering the composition to the mouse; and detecting changes in the phenotype, wherein a change in said phenotype indicates that a composition has modulated the activity of said estrogen receptor.

5. The method of claim 4, wherein expression of the human estrogen receptor gene causes epidermal hyperplasia.

6. The method of claim 4, wherein expression of the human estrogen receptor gene causes erythematous ears.

7. The method of claim 4, wherein said composition is administered topically.

8. The method of claim 4, wherein said composition is administered orally.

9. The method of claim 4, wherein said composition is administered parenterally.

10. The method of claim 4, wherein said changes are detected by visual inspection.

11. The method of claim 4, wherein said changes are detected by microscopic observation.

* * * * *

UNITED STATES PATENT AND TRADEMARK OFFICE
CERTIFICATE OF CORRECTION

PATENT NO. : 6,586,655 B2
DATED : July 1, 2003
INVENTOR(S) : Arbeit et al.

It is certified that error appears in the above-identified patent and that said Letters Patent is hereby corrected as shown below:

<u>Column 1,</u>
Line 4, insert:

-- STATEMENT AS TO RIGHTS TO INVENTIONS MADE UNDER
FEDERALLY SPONSORED RESEARCH AND DEVELOPMENT
      This invention was made with Government support under Grant
No. CA71398, awarded by the National Institutes of Health. The Government
has certain rights in this invention. --

Signed and Sealed this

Fourth Day of November, 2003

JAMES E. ROGAN
*Director of the United States Patent and Trademark Office*